United States Patent
Manley et al.

(10) Patent No.: US 9,814,748 B2
(45) Date of Patent: *Nov. 14, 2017

(54) SYNERGISTIC SALIVATION AGENTS

(71) Applicant: Takasago International Corp. (USA), Rockleigh, NJ (US)

(72) Inventors: Charles Manley, Ringwood, NJ (US); David J. Spence, Rockleigh, NJ (US); Carter B. Green, Stony Point, NY (US)

(73) Assignee: TAKASAGO INTERNATIONAL CORPORATION (USA), Rockleigh, NJ (US)

( * ) Notice: Subject to any disclaimer, the term of this patent is extended or adjusted under 35 U.S.C. 154(b) by 447 days.

This patent is subject to a terminal disclaimer.

(21) Appl. No.: 13/856,060

(22) Filed: Apr. 3, 2013

(65) Prior Publication Data

US 2014/0099391 A1    Apr. 10, 2014

Related U.S. Application Data

(63) Continuation of application No. 11/368,110, filed on Mar. 3, 2006, now Pat. No. 8,435,542.

(60) Provisional application No. 60/594,004, filed on Mar. 3, 2005.

(51) Int. Cl.
| | | |
|---|---|---|
| *A61K 36/28* | (2006.01) | |
| *A61K 36/61* | (2006.01) | |
| *A23G 3/34* | (2006.01) | |
| *A23G 3/36* | (2006.01) | |
| *A23G 3/48* | (2006.01) | |
| *A23G 4/06* | (2006.01) | |
| *A23L 2/02* | (2006.01) | |
| *A23L 2/56* | (2006.01) | |
| *A61K 31/16* | (2006.01) | |
| *A61K 31/194* | (2006.01) | |
| *A61K 36/81* | (2006.01) | |
| *A61K 36/9068* | (2006.01) | |
| *A61K 45/06* | (2006.01) | |
| *A23L 27/00* | (2016.01) | |
| *A23L 27/14* | (2016.01) | |
| *A23L 27/20* | (2016.01) | |
| *A23L 33/105* | (2016.01) | |

(52) U.S. Cl.
CPC .............. *A61K 36/61* (2013.01); *A23G 3/34* (2013.01); *A23G 3/36* (2013.01); *A23G 3/48* (2013.01); *A23G 4/06* (2013.01); *A23G 4/068* (2013.01); *A23L 2/02* (2013.01); *A23L 2/56* (2013.01); *A23L 27/14* (2016.08); *A23L 27/20* (2016.08); *A23L 27/82* (2016.08); *A23L 33/105* (2016.08); *A61K 31/16* (2013.01); *A61K 31/194* (2013.01); *A61K 36/28* (2013.01); *A61K 36/81* (2013.01); *A61K 36/9068* (2013.01); *A61K 45/06* (2013.01); *A23V 2002/00* (2013.01)

(58) Field of Classification Search
CPC ........................................................ A61K 36/28
USPC ...................................................... 424/195.18
See application file for complete search history.

(56) References Cited

U.S. PATENT DOCUMENTS

| | | | |
|---|---|---|---|
| 3,720,762 A | 3/1973 | Hatasa et al. | |
| 4,597,981 A * | 7/1986 | Kastin .................... | A23G 3/38 426/576 |
| 4,639,368 A | 1/1987 | Niazi et al. | |
| 4,820,506 A | 4/1989 | Kleinberg et al. | |
| 4,983,378 A | 1/1991 | Parnell | |
| 5,372,834 A | 12/1994 | Buckholz et al. | |
| 5,545,424 A | 8/1996 | Nakatsu et al. | |
| 6,746,697 B2 | 6/2004 | Wolfson | |
| 6,780,443 B1 * | 8/2004 | Nakatsu ................... | A23G 3/36 424/725 |
| 6,890,567 B2 | 5/2005 | Nakatsu et al. | |
| 6,899,901 B2 * | 5/2005 | Nakatsu ................... | A23G 3/36 424/725 |
| 7,041,311 B2 | 5/2006 | Grainger | |
| 7,776,923 B2 * | 8/2010 | Gatfield ................. | A23G 3/346 514/626 |
| 8,435,542 B2 | 5/2013 | Manley et al. | |
| 2002/0102331 A1 * | 8/2002 | Chang ..................... | A23L 1/304 426/74 |
| 2003/0035833 A1 | 2/2003 | He | |
| 2003/0039731 A1 * | 2/2003 | Dalton ............... | B65D 85/8043 426/433 |
| 2003/0069202 A1 * | 4/2003 | Kern ........................ | A23C 9/13 514/46 |
| 2003/0072842 A1 * | 4/2003 | Johnson ................... | A23G 4/06 426/3 |
| 2003/0118628 A1 | 6/2003 | Tutuncu et al. | |
| 2003/0170322 A1 * | 9/2003 | Kayane .................... | A23G 3/34 424/725 |

(Continued)

FOREIGN PATENT DOCUMENTS

| | | |
|---|---|---|
| CN | 1 128 636 | 8/1996 |
| EP | 0 446 170 | 9/1991 |

(Continued)

OTHER PUBLICATIONS

U.S. Appl. No. 11/638,110, dated Apr. 4, 2013, Issue Fee payment.

(Continued)

Primary Examiner — Chris R Tate
(74) Attorney, Agent, or Firm — Baker Botts L.L.P.

(57) ABSTRACT

Provides is a salivation cocktail that comprises a food acid and a tingling sensate. The combination of a food acid and a tingling sensate has been found to synergistically increase salivation.

13 Claims, No Drawings

(56) References Cited

U.S. PATENT DOCUMENTS

| | | | |
|---|---|---|---|
| 2003/0215532 A1 | 11/2003 | Nakatsu et al. | |
| 2004/0170576 A1 | 9/2004 | Grainger et al. | |
| 2004/0241312 A1 | 12/2004 | Gatfield | |
| 2005/0074533 A1* | 4/2005 | John | A23G 3/346 426/534 |
| 2006/0024246 A1 | 2/2006 | Maitra et al. | |
| 2006/0029665 A1 | 2/2006 | Singh | |
| 2006/0034936 A1* | 2/2006 | Lakkis | A23G 3/36 424/490 |
| 2006/0263475 A1* | 11/2006 | Jani | A23G 4/064 426/3 |
| 2007/0202188 A1 | 8/2007 | Ley et al. | |
| 2008/0014302 A1* | 1/2008 | Elejalde | A23G 4/10 426/5 |
| 2008/0063747 A1* | 3/2008 | Boghani | A23G 4/06 426/5 |
| 2009/0155445 A1 | 6/2009 | Le et al. | |
| 2010/0184863 A1 | 7/2010 | Lombardo et al. | |
| 2011/0105773 A1 | 5/2011 | Tanaka et al. | |
| 2012/0040057 A1 | 2/2012 | Ferri et al. | |
| 2012/0129953 A1 | 5/2012 | Le et al. | |

FOREIGN PATENT DOCUMENTS

| | | |
|---|---|---|
| EP | 1 293 131 A1 | 3/2003 |
| JP | 57-118518 | 7/1982 |
| JP | 62198611 A * | 9/1987 |
| WO | WO 2004/043906 | 5/2004 |
| WO | WO 2005/011811 | 2/2005 |
| WO | WO 2005/044778 | 5/2005 |
| WO | WO 2005/099473 | 10/2005 |

OTHER PUBLICATIONS

U.S. Appl. No. 11/638,110, dated Jan. 4, 2013, Notice of Allowance.
U.S. Appl. No. 11/638,110, dated Oct. 24, 2012, Response to Non-Final Office Action.
U.S. Appl. No. 11/638,110, dated Apr. 24, 2012, Non-Final Office Action.
U.S. Appl. No. 11/638,110, dated Apr. 6, 2012, Applicant Initiated Interview Summary.
U.S. Appl. No. 11/638,110, dated Mar. 22, 2012, Restriction Requirement.
U.S. Appl. No. 11/638,110, dated Jan. 13, 2012, Applicant Initiated Interview Summary.
U.S. Appl. No. 11/638,110, dated Nov. 17, 2011, Restriction Requirement.
U.S. Appl. No. 11/638,110, dated Apr. 26, 2011, Amendment and Request for Continued Examination (RCE).
U.S. Appl. No. 11/638,110, dated Oct. 26, 2010, Final Office Action.
U.S. Appl. No. 11/638,110, dated Aug. 6, 2010, Response to Notice of Non-Compliant.
U.S. Appl. No. 11/638,110, dated Jul. 16, 2010, Notice of Non-Compliant.
U.S. Appl. No. 11/638,110, dated May 10, 2010, Response to Non-Final Office Action.
U.S. Appl. No. 11/638,110, dated Nov. 10, 2009, Non-Final Office Action.
U.S. Appl. No. 11/638,110, dated Aug. 21, 2009, Amendment and Request for Continued Examination (RCE).
U.S. Appl. No. 11/638,110, dated Aug. 17, 2009, Advisory Action.
U.S. Appl. No. 11/638,110, dated May 8, 2009, Final Office Action.
U.S. Appl. No. 11/638,110, dated Feb. 3, 2009, Response to Non-Final Office Action.
U.S. Appl. No. 11/638,110, dated Nov. 3, 2008, Non-Final Office Action.
U.S. Appl. No. 11/638,110, dated Aug. 11, 2008, Amendment and Request for Continued Examination (RCE).
U.S. Appl. No. 11/638,110, dated Jan. 11, 2008, Notice of Appeal.
U.S. Appl. No. 11/638,110, dated Jul. 11, 2007, Final Office Action.
U.S. Appl. No. 11/638,110, dated May 9, 2007, Response to Non-Final Office Action.
U.S. Appl. No. 11/638,110, dated Jan. 9, 2007, Non-Final Office Action.
U.S. Appl. No. 11/638,110, dated Nov. 9, 2006, Response to Restriction Requirement.
U.S. Appl. No. 11/638,110, dated Sep. 26, 2006, Restriction Requirement.
U.S. Appl. No. 12/505,283, dated Dec. 5, 2012, Response to Non-Final Office Action.
U.S. Appl. No. 12/505,283, dated Jun. 5, 2012, Non-Final Office Action.
U.S. Appl. No. 12/505,283, dated Dec. 20, 2011, Response to Restriction Requirement.
U.S. Appl. No. 12/505,283, dated Nov. 28, 2011, Restriction Requirement.
International Search Report and Written Opinion for PCT/US2006/008016, dated Nov. 29, 2006.
Kaneuchi, et al., "Production of Succinic Acid from Citric Acid and Related Acids by *Lactobacillys* Strains", *Applied and Environmental Microbiology*, 54(12):3053-3056 (1988).
Ley, et al., "Structure Activity Relationships of Trigeminal Effects for Artificial and Naturally Occuring Alkamides related to Spilanthol", *11th Weurmann Flavour Research Symposium*, Roskild, Denmark, Jun. 21-24, 2005, 4 pages.
Ramsewak, et al., "Bioactive N-isobutylamides from the flower buds of *Spilanthes acmella*", *Phytochemistry*, 51:729-732 (1999).
European Office Action dated Dec. 22, 2014 in EP Application No. 06769774.8.

\* cited by examiner

SYNERGISTIC SALIVATION AGENTS

CROSS REFERENCE TO RELATED APPLICATION

This application is a continuation of copending U.S. patent application Ser. No. 11/368,110, filed on Mar. 3, 2006, which claims the priority under 35 U.S.C. §119 to U.S. Provisional Application Ser. No. 60/594,004, filed Mar. 3, 2005, both of which are hereby incorporated by reference in their entireties, and to both of which priority is claimed.

FIELD OF THE INVENTION

The present application relates to food or beverage additives that enhance salivation upon consumption of the food or beverage.

BACKGROUND OF THE INVENTION

The term "dry mouth" (a/k/a, xerostomia) describes an oral condition in which salivary production and/or flow is reduced. Dry mouth may result from one or more of a number of underlying conditions. In many cases, for example, dry mouth occurs due to a natural decrease of saliva production that occurs upon aging. The ability to produce saliva by people in their sixties is typically one-eight of that in young adults. Dry mouth may also affect people with speaking or digestive difficulties or result as a side effect of medication, for example medications used to treat depression and other psychiatric conditions. Dry mouth or xerostomia is also associated with rheumatoid arthritis, diabetes, kidney failure, infection with HW (the virus that causes AIDS), trauma to the salivary glands, or their ducts or nerves and radiation treatment for mouth or throat cancer.

A sufficient level of salivation is important for good oral hygiene and taste sensation. Dry mouth is conducive to the growth of microorganisms that cause halitosis or bad breath. Accordingly, many breath freshening products include formulations that increase saliva flow in the oral cavity. Dry mouth decreases taste sensation and, thus, may decrease the ability to taste and enjoy food and beverages. Increased saliva flow, conversely, promotes taste sensation and, thus, may increase the ability to taste and enjoy foods and beverages.

Unfortunately, ingredients added to increase salivation in the food or beverages often cause the food or beverage to have an unpleasant taste. There remains a need for salivation component(s) that are effective to increase salivation without negatively affecting the taste of the product to which the salivation agent is added. Similarly, there remains a need for more effective salivation components(s) so that salivation is increased at lower use levels. There is also a need for improved treatment of subjects who suffer from xerostomia, and to inhibit xerostomia in those subjects who have, or at risk of developing this condition.

SUMMARY OF THE INVENTION

The present application relates to compositions comprising a) a food acid and ii) a tingling sensate. The compositions pleasing have a pleasant taste and promote salivation in products to which they have been added, such as foods, and beverages.

In one embodiment of the present application, the tingling sensate is selected from spilanthol, sanshool, hydroxy α-sanshool, hydroxy β-sanshool, hydroxy γ-sanshool, sanshool I, sanshool II, sanshoamide, japanese pepper extract, black pepper extract, chavicine, piperine, echinacea extract, northern prickly ash extract, Nepalese spice timur extract, red pepper oleoresin, 4-(1-menthoxymethyl)-2-phenyl-1,3-dioxolane and jambu oleoresin. In a preferred embodiment, the tingling sensate is spilanthol that is obtained from jambu oleoresin.

In another embodiment of the present application, the food acid is selected from acetic acid, adipic acid, aspartic acid, benzoic acid, caffeotannic acid, citric acid, iso-citric acid, citramalic acid, formic acid, fumaric acid, galacturonic acid, glucuronic acid, glyceric acid, glycolic acid, ketoglutaric acid, α-ketoglutaric acid, lactic acid, lactoisocitric acid, malic acid, oxalacetic acid, oxalic acid, pyruvic acid, quinic acid, shikimic acid, succinic acid, tannic acid, and tartaric acid. In a preferred embodiment, the food acids is selected from citric acid, lactic acid, malic acid, succinic acid, fumaric acid, tartaric acid, ascorbic acid or adipic acid. In a particularly preferred embodiment, the food acid is succinic acid.

The present application also provides a method of increasing the salivation effect of a food or beverage when consumed by a human comprising or consisting essentially of, the step of adding (a) a food acid and (b) a tingling sensate to the food or beverage. Examples of foods or beverages in which the salivation cocktail may be added include, but are not limited to, carbonated fruit beverages, sport beverages, carbonated cola drinks, wine coolers, cordials, flavored water, powders for drinks, hard candy, soft candy, taffy, chocolates, sugarless candies, chewing gum, bubble gum, condiments, spices and seasonings, dry cereal, oatmeal, granola bars, alcoholic beverages, energy beverages, juices, teas, coffees, salsa, gel beads, film strips for halitosis, gelatin candies, pectin candies, starch candies, lozenges, cough drops, throat lozenges, throat sprays, toothpastes and mouth rinses.

The present application also provides a method of treating, and a method of inhibiting xerostomia comprising administering a food, beverage, candy, or pharmaceutical dosage form that includes one of the salivation cocktails described in this application to a subject in need thereof. The application also provides for the use of a food, beverage, candy, or pharmaceutical dosage form that includes one of the salivation cocktails described in this application to treat or inhibit xerostomia. The present application also provides for the use of any of the salivation cocktails described in the this application in the manufacture of a medicament for use in treating or inhibiting xerostomia in a subject.

DETAILED DESCRIPTION

It has been found that the salivation effect of a tingling sensate (e.g., spilanthol) is synergistically enhanced when it is combined with a food acid. Accordingly, significantly lower amounts of tingling sensate are necessary to achieve a similar or even an increased salivation effect when combined with a food acid. While it was previously known that common food acids (e.g., citric acid, lactic acid, malic acid, succinic acid, fumaric acid, tartaric acid, ascorbic acid and adipic acid) and jambu oleoresin, individually, can increase salivation, it was not known that the combination of a food acid and a tingling sensate such as spilanthol synergistically increase salivation. Due to the synergistic combination, the combined use level of the salivation cocktail can be made lower than would otherwise be predicted if the effects of the food acid and tingling sensate were merely additive.

In addition to the increased synergistic salivation affect achieved by combining a food acid and a tingling sensate (e.g., spilanthol), the combination also maintains the appealing taste of the food or beverage to which the salivation cocktail is added. This is surprising given that when both of these components are present in a food or beverage alone, the additive usually causes an undesirable off-note or taste (e.g., a food or beverage with green or oily notes). When combined, however, the food acid and tingling sensate do not deteriorate the taste of the food or beverage to which it is added.

Additionally, when sodium or potassium salts of the food acids are employed, they provide the consumer with a source to replace nutrients lost upon perspiration. Accordingly, the combination of sodium or potassium salts of food acid and tingling sensate (e.g., spilanthol) can be added to a sports hydrating drink or powder or to an energy drink or powder to provide a beverage that will prevent dry mouth, taste good, and replenish nutrients lost upon perspiration.

Food Acids

Food acids can be obtained from nuts, fruits and vegetables, including apples, apricots, avocados, bananas, blackberries, blueberries, boysenberries, cherries, cranberries, currants, figs, gooseberries, grapefruits, grapes, lemons, limes, oranges, peaches, pineapples, plums, strawberries, raspberries, beans, broccoli, carrots, mushrooms, peas, potatoes, rhubarbs, and tomatoes. In one embodiment, the food acid is an acid that is the principal acid present in the food (e.g., a fruit or vegetable). Food acids are also commercially available (e.g., from. Unilex Exports Ltd., Mumbai, India).

Examples of food acids that may be used in salivation cocktails include, but are not limited to, acetic, adipic, aspartic, benzoic, caffeotannic acid, citric (including isocitric), citramalic, formic, fumaric, galacturonic, glucuronic, glyceric, glycolic, ketoglutaric (including α-ketoglutaric), lactic, lactoisocitric, malic, oxalacetic, oxalic, pyruvic, quinic, shikimic, succinic acid, tannic, and tartaric acids. Additional food acids may be found in the Source Book of Flavors, AVI Publishing Company Inc. (1981), which is hereby incorporated by reference.

In certain preferred embodiments, a food acid is at least one of citric, lactic, malic, succinic, fumaric tartaric, ascorbic, or adipic acid. In another embodiment, the food acid is selected from citric, malic, tartaric and succinic acid. In one embodiment, the food acid is succinic acid. In another embodiment, the food acid is not citric and/or malic acid.

Tingling Sensates

Examples of tingling sensates that may be used salivation cocktails include, but are not limited to, spilanthol, sanshool, hydroxy α-sanshool, hydroxy β-sanshool, hydroxy γ-sanshool, sanshool I, sanshool II, sanshoamide, piperine, chavicine, 4-(1-menthoxymethyl)-2-phenyl-1,3-dioxolane, effervescing agents and analogs thereof. Other tingling sensates can be found in U.S. Pat. No. 5,545,424 which is herein incorporated by reference.

Various extracts can also be employed as tingling sensates in accordance with the present application. Oftentimes these extracts contain active ingredients which give the extract itself its tingling character. For example, jambu oleoresin extract, obtained from a green leafy plant native to Southeast Asia (*Spilanthes acmelia*, Oleracea) contains spilanthol. Other examples of extracts that can employed as tingling sensates include, but are not limited to, Japanese pepper extract (*Zanthaxylum peperitum*), black pepper extract (*Piper nigrum*), echinacea extract, northern prickly ash extract, Nepalese spice timur extract, and red pepper oleoresin.

In one embodiment the tingling sensate is selected from spilanthol, sanshool and α-hydroxysanshool (timurol). In a preferred embodiment, the tingling sensate is spilanthol, which is employed via use of jambu oleoresin extract (also referred to as jambu oleoresin). Jambu oleoresin is commercially available from Takasago International Corporation (USA), (Rockleigh, N.J.). In one embodiment, the tingling sensate is not sanshool, i.e. sanshool is excluded from amongst the list of possible tingling sensates.

In one embodiment, the tingling sensate contains a compound represented by the formula:

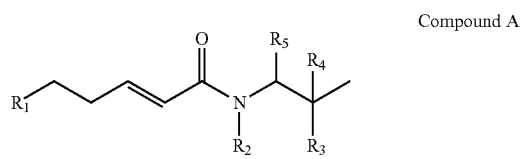

Compound A wherein $R_1$ is a branched or unbranched $C_2$-$C_{10}$ alkenyl group having one or more double bonds which may be conjugated or unconjugated;

$R_2$ is H or $C_1$-$C_6$ alkyl; and $R_3$, $R_4$, and $R_5$ are independently H, $C_1$-$C_6$ alkyl or hydroxy.

In a preferred embodiment of Compound A, $R_1$ is an unbranched $C_2$-$C_{10}$ alkenyl group having conjugated double bonds, preferably an unsubstituted $C_4$-$C_6$ alkenyl group having conjugated double bonds, $R_2$ is H, at least one of $R_3$ or $R_4$ is methyl or hydroxy, and $R_5$ is hydrogen.

Preferred tingling sensates encompassed by formula B include sanshool, α-hydroxy sanshool and spilanthol.

In another embodiment, the tingling sensate is represented by the formula:

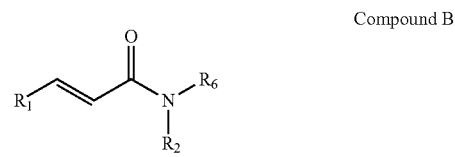

Compound B wherein $R_1$ is a branched or unbranched alkenyl group having one or more double bonds which may be conjugated or unconjugated;

$R_2$ is H or $C_1$-$C_6$ alkyl; and $R_6$ is $C_1$-$C_8$ a branched or unbranched alkyl group, wherein the alkyl group may form a cycloalkyl ring.

In a preferred embodiment of Compound B, $R_1$ is an unsubstituted $C_6$-$C_{10}$ alkenyl group, more preferably a $C_7$-$C_9$ alkenyl group, $R_2$ is H and $R_6$ is a $C_2$-$C_4$ alkyl group. In one embodiment, $R_6$ is a cyclopropyl group.

Preferred tingling sensates represented by compound B include N-Isobutyldeca-Trans-2-Trans-4-dienamide (pellitorin), n-cyclopropyl, trans-2-cis-6-nonadienamide, and n-ethyl trans-2-cis-6-nonadienamide.

Compositions of Food Acids and Tingling Sensates

In preferred embodiments, the present invention provides compositions comprising at least one food acid and at least one tingling sensate that are included in a salivation cocktail. Preferably, the salivation cocktail consists essentially of the at least one food acid and the at least one tingling sensate. In certain embodiments, the salivation cocktail is added to a food, beverage, oral personal care product, gum, candy or lozenge. The salivation cocktail can contain more than one food acid and/or tingling sensate.

The components of the salivation cocktail can be combined and then added to the food or beverage, or the components can be added separately to the food or beverage. In either case, the combination of the at least one food acid and the at least one tingling sensate is referred to as the salivation cocktail.

In one embodiment, the salivation cocktail comprises, or consists essentially of, a food acid selected from citric, lactic, malic, succinic, fumaric, tartaric, ascorbic, or adipic acid and a tingling sensate selected from spilanthol, sanshool and α-hydroxysanshool (timourol). In one embodiment, the salivation cocktail comprises, or consists essentially of, succinic acid and spilanthol. In another embodiment, the salivation cocktail comprises, or consists essentially of, succinic acid and jambu oleoresin (which contains spilanthol as its principal active ingredient).

In one embodiment of the present invention, the salivation cocktail is added to pharmaceutical dosage forms (e.g., a tablet, capsule, drops or lozenges) which contains a medicament. For example, one embodiment of the present invention provides a cough drop or lozenge containing a) menthol or other medicaments for the treatment of sore throat, coughing or other upper respiratory ailments and b) one of the salivation cocktails described in this application. In another embodiment, a salivation cocktail of the present application is added to a pharmaceutical dosage form which contains an active agent (e.g. an anti-depressant) that typically induces xerostomia as a side effect.

In other embodiments of the present invention, the salivation cocktail is the only medicament included in the composition, and the composition is used to treat or inhibit xerostomia in a subject in need thereof. For example, a salivation agent may administered to a subject to alleviate the symptoms of Sjogren's Syndrome, Rheumatoid Arthritis or other condition in which xerostomia is a symptom. The salivation cocktail is added to a food, beverage or pharmaceutical dosage form expressly for the purpose of administration to a subject who suffers from xerostomia. In such embodiments, it is preferable that the composition be free of other medicaments or agents that cause or contribute to xerostomia.

In one embodiment of the present invention, the salivation cocktail composition is in a form suitable for introduction to a food or beverage for the general public. A composition is not in a form suitable for introduction to a food or beverage for the general public when it contains a medicament for the treatment of any physiological condition, ailment and/or disease (except dry mouth), such as decongestants or anorexics (e.g. phenyl propanolamine). For purposes of this embodiment, any of the aforementioned tingling sensates (e.g. spilanthol or sanshool) or food acids (eg. citric acid), singularly or combined, are not considered a medicament since the general public is presumed to have relatively normal salivation levels, and the salivation cocktail is added to supplement these normal levels of salivation for hedonistic purposes (e.g., to make food taste better). A composition is also not in a form suitable for introduction to a food or beverage for the general public when it contains exotic ingredients such as powder from liver, lungs, heart, kidneys, spleen or other organs, since the inclusion of these components in foods or beverages would not be hedonistically appealing to the general public. For example, the compositions disclosed in U.S. Pat. No. 4,639,368 and Japanese Publication No. 57-118518 are compositions that are not in a form suitable for introduction to a food or beverage for the general public.

In one embodiment of the present application, the compositions include all the compositions disclosed in the present application, except that all the compositions disclosed in U.S. Pat. No. 4,639,368 and Japanese Publication No. 57-118518 are excluded. These patents and applications are hereby incorporated by reference.

Use levels of the salivation cocktail (food acid plus tingling sensate) may range from about 0.01% or 0.1% to about 1% or 5%, or from about 0.05% or 0.1% to about 0.3% or 1%, or from about 0.035% or 0.07% to about 0.125% or 0.25%, or from about 0.1% to about 0.2% based on the total weight of the food or beverage. In one embodiment, the use level of salivation cocktail is about 0.12%. For beverages, the above percentages are by volume of the salivation cocktail, based on the total volume of the beverage batch (v/v). For foods, the above percentages are by volume of the salivation cocktail, based on the total weight of the food batch (v/w).

The volume ratio of food acid to tingling sensate in the salivation cocktail may range from about 100:1 or 50:1 to about 1:50 or 1:100 or from about 50:1 or 25:1 to about 5:1 or 1:1. In one embodiment, the volume ratio of food acid to tingling sensate ranges from about 7:1 or 11:1 to about 12:1 or 15:1. In one embodiment, the ratio of food acid to tingling sensate is about 11.7:1. In the above ratios, the amount of tingling sensate refers to the volume of the active ingredient, not the volume of extract (e.g., jambu oleoresin) from which the active ingredient (e.g., spilanthol) is obtained.

The salivation cocktails described above can be added to, for example, compositions for the preparation of carbonated fruit beverages, carbonated cola drinks, wine coolers, cordials, flavored water, powders for drinks (e.g., powdered sports or "hydrating" drinks), hard candy, soft candy, taffy, chocolates, sugarless candies, chewing gum, bubble gum, condiments, spices and seasonings, dry cereal, oatmeal, granola bars, alcoholic beverages, energy beverages, juices, teas, coffees, salsa, gel beads, film strips for halitosis, gelatin candies, pectin candies, starch candies, lozenges, cough drops, throat lozenges, throat sprays, toothpastes and mouth rinses. Use levels of salivation cocktails and relative amounts of food acids and tingling sensates can be adjusted by persons of ordinary skill in the art depending of the flavor of the additives employed in the end use food or beverage, or the taste or flavor of the end product itself. In one embodiment, chewing gum and bubble gum are excluded from the possible foods or beverages which the salivation agent may be added.

EXAMPLES

The following examples illustrate the invention without limitatjon.

Example 1

A carbonated citrus beverage may be prepared with the ingredients shown below:

| Ingredients | Amounts |
| --- | --- |
| High Fructose Corn Syrup | 855 grams |
| Sodium Benzoate | 1.80 grams |
| Citric Acid | 7.50 grams |

-continued

| Ingredients | Amounts |
|---|---|
| Sodium Citrate (25% aqueous solution, commercially available from Takasago) | 0.90 ml |
| Natural Citrus Flavor with other natural flavors ("WONF") (commercially available from Takasago) | 15.00 ml |
| Salivation Cocktail | 1.20 ml |
| Water QS to Yield | 1000.00 ml |

Finished Product Specifications: Brix: 10.6

The Salivation Cocktail has the following composition:

| Ingredient | Amount (vol %) |
|---|---|
| Propylene glycol | 95.36 |
| Succinic Acid | 3.50 |
| Jambu Oleoresin (containing 30 vol % Spilanthol) (commercially available from Takasago) | 1.00 |
| Capsicum Oleoresin (commercially available from Kalsec Inc., Kalamazoo, MI) | 0.02 |
| Ginger Oleoresin (commercially available from Kalsec Inc., Kalamazoo, MI) | 0.12 |

Example 2

A Diet Cola Carbonated Beverage may be prepared with the ingredients shown below:

| Ingredients | Amounts |
|---|---|
| Aspartame | 1.50 grams |
| Sodium Benzoate 25% solution (w/v) | 3.00 ml |
| Phosphoric Acid, 85% solution | 0.70 ml |
| Citric Acid, 50% solution (w/v) | 0.50 ml |
| Anhydrous Caffeine | 0.40 grams |
| Caramel Color DS400 (commercially available from Sethness, Lincolnwood, IL) | 1.50 ml |
| Natural Cola Flavor WONF (commercially available from Takasago) | 3.90 ml |
| Salivation Cocktail of Example 1 | 0.6 ml |
| Water QS to Yield | 500.00 ml |

Carbonation: 3.5 Vol. This syrup may be used to make 3 L of a finished beverage.

Example 3

A cranberry apple flavored still beverage containing 3% Juice may be prepared from the ingredients shown below:

| Ingredients | Amounts |
|---|---|
| High Fructose Corn Syrup SS, 76 brix | 135.00 grams |
| Cranberry Juice Concentrate, 50 brix | 4.65 grams |
| Tartaric Acid, 50% Solution | 1.75 ml |
| Citric Acid, 50% Solution | 1.75 ml |
| Ascorbic Acid | 0.30 grams |
| Salivation Cocktail of Example 1 | 1.2 ml |
| Tannic Acid | 0.04 grams |
| Natural Cranberry Flavor WONF (commercially available from Takasago) | 3.20 ml |
| Natural Apple Flavor WONF (commercially available from Takasago) | 0.25 ml |

-continued

| Ingredients | Amounts |
|---|---|
| FD&C Red 40, 1% Solution (commercially available from Sensient Technologies Corporation, Milwaukee, WI) | 1.77 ml |
| FD&C Blue 1, 0.1% Solution | 1.60 ml |

Pasteurize at 190-195° F. for 1-2 minutes
Brix ~10.80 ± 0.10
pH ~2.5 ± 0.10
Vitamin C - 100%/8 oz serving

Example 4

A 10 Proof Carbonated Cooler [Plum Type Flavor] may be prepared from the ingredients shown below:

| Ingredients | Amounts |
|---|---|
| Distilled Vodka 100 Proof | 300.00 ml |
| Sucrose, granulated | 285.00 g |
| Sodium Citrate (anhydrous) | 3.00 g |
| Sodium Benzoate, 25% soln (w/v) | 3.60 ml |
| Malic Acid, 50% soln. (w/v) | 21.00 ml |
| Salivation Cocktail of Example 1 | 1.2 ml |
| Natural Flavor Plum Type (commercially available from Takasago) | @0.05% |
| Natural Rose Flavor WONF (commercially available from Takasago) | @0.02% |
| FD& C Red 40, 1% soln, (commercially available from Sensient Technologies Corporation, Milwaukee, WI) | @0.05% |
| FDC Blue, 1, 0.1% soln. (commercially available from Sensient Technologies Corporation, Milwaukee, WI) | @0.10% |
| Q.S. with water to | 1000.00 ml |

This syrup may be used to make 3 L of finished product

Example 5

A 35 Proof Cordial [Raspberry Type Flavor] may be prepared from the ingredients shown below:

| Ingredients | Amounts |
|---|---|
| Distilled Vodka 100 Proof | 350.00 ml |
| Sucrose, granulated | 250.00 g |
| Malic Acid, 50% soln. (w/v) | 10.00 ml |
| Salivation Cocktail of Example 1 | 1.20 ml |
| VIVID FL ™ Nat. Raspberry Flavor (commercially available from Takasago) | @0.05% |
| FD&C Red 40, 1% soln. (commercially available from Sensient Technologies Corporation, Milwaukee, WI) | @0.15% |
| FD&C Blue, 1, 0.1% soln. (commercially available from Sensient Technologies Corporation, Milwaukee, WI) | @0.15% |
| Q.S. with water to | 1000.00 ml |

Example 6

A 60 Proof Cordial [Cherry Type Flavor] may be prepared from the ingredients shown below:

| Ingredients | Amounts |
|---|---|
| Distilled Vodka 100 Proof | 600.00 ml |
| Sucrose, granulated | 270.00 g |
| Glycerin | 15.00 ml |

-continued

| Ingredients | Amounts |
| --- | --- |
| Malic Acid, 50% soln. (w/v) | 5.00 ml |
| Salivation Cocktail of Exampe 1 | 1.2 ml |
| Natural and Artificial Cherry Flavor (commercially available from Takasago) | @0.08% |
| Q.W. with water to | 1000.00 ml |

Example 7

A flavored water (Nat. Sweetened) [Strawberry Flavor Type] may be prepared from the ingredients shown below:

| Ingredients | Amounts |
| --- | --- |
| Apple Juice Concentrate, 70 brix (12%) | 20.60 g |
| Natural Flavor Sweet Sugar Type (commercially available from Takasago) | 0.50 ml |
| Salivation Cocktail of claim 1 | 1.2 ml |
| VIVID Flavor ™ Nat. Wild Strawberry Flavor WONF (commercially available from Takasago) | @0.10% |
| VIVID Flavor ™ Nat. Strawberry Flavor WONF (commercially available from Takasago) | @0.05% |
| Q.S. with water to | 1000.00 ml |

Pasteurize at 190-195° F. for 1-2 minutes.
Brix: 1.60 ± 0.10
pH: 3.40 ± 0.10
20 calories/8 oz serving Example 8

A flavored water (Sweetened w/Sucralose) [Lemon Strawberry Type] may be prepared from the ingredients shown below:

| Ingredients | Amounts |
| --- | --- |
| Apple Juice Concentrate, 70 brix (12%) (commercially available from Takasago) | 20.60 g |
| Natural Fl Sweet Sugar Type (commercially available from Takasago) | 0.50 ml |
| Sucralose 25% Soln. | 0.10 ml |
| Salivation Cocktail of Example 1 | 1.2 ml |
| Natural Juicy Lemon Fl WONF (commercially available from Takasago) | @0.05% |
| Natural Strawberry Fl WONF (commercially available from Takasago) | @0.20% |
| Q.S. with water to | 1000 ml |

Pasteurize at 190-195° F. for 1-2 minutes
Brix: 1.60 ± 0.10
pH: 3.40 ± 0.10
20 calories/8 oz. serving Example 9

A powdered hydrating mix may be prepared from the ingredients shown below:

| Ingredients | Amounts |
| --- | --- |
| Dextrose | 75.09 g |
| Potassium Citrate | 8.21 g |
| Salt | 6.60 g |
| Sodium Citrate | 4.00 g |
| Tartaric Acid | 5.20 g |
| Salivation Cocktail of Example 1 | 0.12 ml |
| Ace-K | 0.60 g |
| Sucralose | 0.18 g |
| Flavor QS to | 100.0 g |

Usage: 6.2 g per 6 oz. of water

Example 10

A hard candy may be prepared from the ingredients shown below:

| Ingredients | Amounts |
| --- | --- |
| Corn Syrup 42DE | 35.0 g |
| Sugar | 52.0 g |
| Nat. Cola Flavor WONF (commercially available from Takasago) | 0.002 g |
| Citric Acid | 0.002 g |
| Salivation Cocktail of Example 1 | 0.12 ml |
| Water QS to | 100.0 g |

Cook to approx. 300° F., cool down to about 240-280° F. Add other ingredients such as flavor and acid, etc. deposit in candy mold to form pieces. Corn syrup and sugar ratio may vary depending on manufacturing requirement.

Example 11

A sugarless candy formula may be prepared from the ingredients shown below:

| Ingredients | Amounts |
| --- | --- |
| Iso-malt | 98.5 g |
| Art.Watermelon Flavor WONF (commercially available from Takasago) | 0.5 g |
| Citric Acid | 0.5 g |
| Malic acid | 0.5 g |
| Salivation Cocktail of Example 1 | 0.12 ml |
| Water QS to | 100.0 g |

Cook iso-malt or other sugar alcohols [e.g., sorbitol, mannitol, malitol, etc.] to their corresponding melting temperatures with a small amount of water, cool down to about 240-280° F., adding other ingredients such as flavor, acid, color, etc. deposit in candy mold to form pieces.

Example 12

A chewing gum may be prepared from the ingredients shown below:

| Ingredients | Amounts |
| --- | --- |
| Gum base | 20.0 g |
| Corn Syrup | 20.0 g |
| Water | 0.24 g |
| Glycerin | 0.24 g |
| Salivation Cocktail | 0.12 g |
| Flavor | 1.0 g |
| Citric Acid | 1.0 g |
| Confectioners sugar QS to | 100.0 g |

Example 13

Four batches of grapefruit mint hard candy were prepared. The first batch (Batch A) contained 0.5% (by volume of grapefruit flavor. The second, third, and fourth batches of grapefruit mint hard candy also contained 0.5% by volume of grapefruit flavor. Additionally, the second batch (Batch 13) contained 0.65% by volume of salivation cocktail set forth below in which jambu oleoresin is the only salivation component:

| Ingredient | Amount (vol %) |
| --- | --- |
| Propylene glycol | 98.86 |
| Jambu Oleoresin (containing 30 wt % Spilanthol) (commercially available from Takasago) | 1.00 |
| Capsicum Oleoresin (commercially available from Kalsec Inc., Kalamazoo, MI) | 0.02 |
| Ginger Oleoresin (commercially available from Kalsec Inc., Kalamazoo, MI) | 0.12 |

In addition to the grapefruit flavor, the third batch (Batch C) contained a salivation cocktail shown below in which succinic acid is the only salivation component:

| Ingredient | Amount (vol %) |
| --- | --- |
| Propylene glycol | 96.36 |
| Succinic acid | 3.5 |
| Capsicum Oleoresin (commercially available from Kalsec Inc., Kalamazoo, MI) | 0.02 |
| Ginger Oleoresin (commercially available from Kalsec Inc., Kalamazoo, MI) | 0.12 |

In addition to the grapefruit flavor, the third batch (Batch D) contained a salivation cocktail described in Example 1 containing a synergistic combination of succinic acid and spilanthol obtained from jambu oleoresin.

Batches A (flavor only), B (flavor+jambu oleoresin), C (flavor+succinic acid) and D (flavor+succinic acid+jambu oleoresin) were orally administered to three panels of six trained sensate experts. The panelists collected their saliva in a cup over the 5 minute collection period (the "drool test"). The panelists also rated the salivation intensity of the sample on a scale of 1-10 at 30 sec, and 1, 2, 3, 4 and 5 min after administration ("salivation intensity"). Panelist also rated their "overall liking" of the sample on a scale of 1 (lowest)-7 (highest). Panelists also provided their comments on the taste and salivation effect of the administered sample.

The results of the drool test for each panelist are set forth below:

| Panelist | Salivation amount (grams) -- Batch A (flavor only) | Salivation amount (grams) -- Batch B (flavor + jambu oleoresin) | Salivation amount (grams) -- Batch C (flavor + succinic acid) | Salivation amount (grams) -- Batch D (flavor + jambu oleoresin + succinic acid) |
| --- | --- | --- | --- | --- |
| 1 | 12.68 | 18.37 | 18.15 | 18.93 |
| 2 | 16.55 | 15.31 | 17.33 | 19.11 |
| 3 | 27.30 | 27.20 | 27.9 | 30.73 |
| 4 | 21.61 | 15.20 | 14.89 | 19.80 |
| 5 | 14.90 | 18.03 | 16.32 | 18.29 |
| 6 | 19.49 | 18.36 | 17.45 | 24.60 |
| Panel Average | 18.76 | 18.74 (−0.02 g -- compared to A) | 18.67 (−0.09 g -- compared to A) | 21.91 (+3.15 -- compared to A) |
| Panel Average Excluding Panelist 4 | 18.18 | 19.45 (+1.27 g -- compared to A) | 19.43 (+1.25 g -- compared to A) | 22.33 (+4.15 g -- compared to A) |

The panel's average results for the Salivation Intensity Test at the set forth below (1=lowest, 9=highest)

| Time Interval | Salivation Intensity -- Batch A (flavor only) | Salivation Intensity -- Batch B (flavor + jambu oleoresin) | Salivation Intensity -- Batch C (flavor + succinic acid) | Salivation Intensity -- Batch D (flavor + jambu oleoresin + succinic acid) |
| --- | --- | --- | --- | --- |
| 30 seconds | 3.73 | 4.67 | 4.23 | 4.87 |
| 1 minute | 4.04 | 4.97 | 4.53 | 5.12 |
| 2 minutes | 3.99 | 5.37 | 4.58 | 5.05 |
| 3 minutes | 3.91 | 5.70 | 4.47 | 4.90 |
| 4 minutes | 3.79 | 5.93 | 4.27 | 4.98 |
| 5 minutes | 3.57 | 5.73 | 3.97 | 4.98 |
| Average over 5 minute test | 3.84 | 5.40 | 4.34 | 4.98 |

The panel's average results for the "overall liking" of the grapefruit mint candy is set forth below (1=lowest, 7=highest)

| Time Interval | Overall Liking -- Batch A (flavor only) | Overall Liking -- Batch B (flavor + jambu oleoresin) | Overall Liking -- Batch C (flavor + succinic acid) | Overall Liking -- Batch D (flavor + jambu oleoresin + succinic acid) |
|---|---|---|---|---|
| 2 minutes | 4.0 | 4.2 | 4.3 | 4.5 |

Panelist were administered Batch A as a control and either Batch B, C, or D. The panelist offered the following qualitative comments for the respective batches after five minutes:

Batch A (Flavor Only) and Batch B (Flavor+Jambu Oleoresin)

| Panelist | Batch | Comment |
|---|---|---|
| 1 | A | "this sample had pretty good salivation" "it increased gradually" |
| 2 | A | "not as salivating" |
| 3 | A | "moderate salivation at the beginning that gradually lessened" |
| 4 | A | "moderate salivation" "nice flavor" |
| 5 | A | "initial medicinal taste" |
| 6 | A | "weak salivation" |
| 1 | B | "salivation effect was high but I could taste the jambe and my tongue is . . . confused" |
| 2 | B | "pretty good salivation" "could feel tingle" |
| 3 | B | "strong salivation maintained throughout five minutes" "tingling, slightly burning sensation" |
| 4 | B | "good salivation, but tingle too high" |
| 5 | B | "too much jambu" |
| 6 | B | "medium to strong salivation" |

Batch A (Flavor Only) and Batch C (Flavor+Succinic Acid)

| Panelist | Batch | Comment |
|---|---|---|
| 1 | A | "good salivation, but slimy mouthfeel" |
| 2 | A | "didn't really get a perception of salivation in this sample" "if [salivation perception] was there it was slight" |
| 3 | A | "initial flavor was harsh and bitter" "after [harshness/bitterness] subsided I noticed the salivation was only moderate, increasing only slightly as time progressed" |
| 4 | A | "somewhat bitter, decent salivation" |
| 5 | A | "felt like the baseline salivation that I would experience" |
| 6 | A | "not overly impressed with salivation" |
| 1 | C | "good salivation" |
| 2 | C | "didn't have much of a salivation effect" "salivation I got I think was just from the candy and the slight cooling and bitterness in it" |
| 3 | C | "more pleasant flavor than other sample" "salivation was stronger than other sample - maintained pretty much throughout the whole time period" |
| 4 | C | "minor salivation, not so good" |
| 5 | C | "no unusual salivation experienced" |
| 6 | C | "slight bitter taste" |

Batch A (Flavor Only) and Batch D (Flavor+Jambu Oleoresin+Succinic Acid)

| Panelist | Batch | Comment |
|---|---|---|
| 1 | A | "not nearly as salivacious" |
| 2 | A | "salivation died off" |
| 3 | A | "nothing special" |
| 4 | A | "salivation started slow, then increased, then quickly died" |
| 5 | A | "low salivation" |
| 6 | A | "sample intensity stayed pretty much same and started decreasing at the end" "slight irritation in the throat but that may have been due to the flavor itself" |
| 1 | D | "salivation was strong from the beginning and maintained throughout the five minutes" |
| 2 | D | "excellent salivatiousness!" "good stuff" |
| 3 | D | "citrus minty and salavicious" |
| 4 | D | "not very salivating" |
| 5 | D | "great salivation" |
| 6 | D | "the intensity of the sample was much higher" "tongue still tingling and my throat didn't get irritated like it did with the first sample" "this sample had even better taste than the first" |

The results of these examples, including the drool test, show that the increase in salivation caused by Batch D (jambu oleoresin+succinic acid) is synergistic as compared to the increase in salivation caused by Batch B (jambu oleoresin) and Batch C (succinic acid only). The comments of the panelist and the quantitative overall liking scale indicates that the combined use of the jambu oleoresin and succinic acid provided a hard candy that tasted better than the candy with flavor alone, or the candy with jambu oleoresin or succinic acid alone.

The above-mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

What is claimed is:

1. A salivation cocktail composition consisting essentially of (a) tartaric acid and (b) spilanthol;
   wherein the tartaric acid and the spilanthol are present in an effective amount such that human salivation is synergistically increased upon consumption of the salivation cocktail, and the volume ratio of the tartaric acid to the spilanthol in the cocktail is from about 5:1 to about 25:1.

2. The salivation cocktail composition of claim 1, wherein the spilanthol is obtained from jambu oleoresin.

3. The salivation cocktail composition of claim 1, wherein the food acid is obtained from a fruit or vegetable.

4. The salivation cocktail of claim 1, wherein the volume ratio of the tartaric acid to the spilanthol in the cocktail is from about 7:1 to about 15:1.

5. A food or beverage for the general public comprising a salivation cocktail comprising:

(a) tartaric acid; and
(b) spilanthol;
wherein the tartaric acid and the spilanthol are present in an effective amount such that human salivation is synergistically increased upon consumption of the food or beverage, and the volume ratio of the tartaric acid to the spilanthol in the cocktail is from about 5:1 to about 25:1.

6. The food or beverage of claim 5, wherein the spilanthol is obtained from jambu oleoresin.

7. A food or beverage containing an effective amount of the salivation cocktail of claim 1.

8. The food or beverage of claim 7, wherein the food or beverage is selected from the group consisting of carbonated fruit beverages, sport beverages, carbonated cola drinks, wine coolers, cordials, flavored water, powders for drinks, hard candy, soft candy, taffy, chocolates, sugarless candies, chewing gum, bubble gum, condiments, spices, seasonings, dry cereal, oatmeal, granola bars, alcoholic beverages, energy beverages, juices, teas, coffees, salsa, gel beads, film strips for halitosis, gelatin candies, pectin candies, starch candies, lozenges, cough drops, throat lozenges, throat sprays, toothpastes, mouth rinses and combinations thereof.

9. A method of increasing the salivation effect of a food or beverage when consumed by a human comprising the step of adding an effective amount of the salivation cocktail composition of claim 1 to the food or beverage.

10. The method of claim 9, wherein the components of the salivation cocktail are added to the food or beverage in one step.

11. The method of claim 9, wherein the components of the salivation cocktail are added to the food or beverage in separate steps.

12. The method of claim 9, wherein the food or beverage is selected from carbonated fruit beverages, sport beverages, carbonated cola drinks, wine coolers, cordials, flavored water, powders for drinks, hard candy, soft candy, taffy, chocolates, sugarless candies, chewing gum, bubble gum, condiments, spices, seasonings, dry cereal, oatmeal, granola bars, alcoholic beverages, energy beverages, juices, teas, coffees, salsa, gel beads, film strips for halitosis, gelatin candies, pectin candies, starch candies, lozenges, cough drops, throat lozenges, throat sprays, toothpastes and mouth rinses.

13. A method of treating or inhibiting xerostomia comprising administering a food, beverage or pharmaceutical dosage form that includes an effective amount of the salivation cocktail of claim 1 to a subject in need thereof.

* * * * *